United States Patent
Trappler et al.

(10) Patent No.: US 11,054,185 B1
(45) Date of Patent: Jul. 6, 2021

(54) APPARATUS FOR LYOPHILIZATION OF PRODUCTS CONTAINED IN PRODUCT DELIVERY UNITS

(71) Applicant: Lyophilization Technology, Inc., Ivyland, PA (US)

(72) Inventors: Edward H. Trappler, Langhorne, PA (US); Michael S. Thomas, Holland, PA (US)

(73) Assignee: Lyophilization Technology, Inc., Ivyland, PA (US)

( * ) Notice: Subject to any disclaimer, the term of this patent is extended or adjusted under 35 U.S.C. 154(b) by 0 days.

(21) Appl. No.: 16/799,134

(22) Filed: Feb. 24, 2020

(51) Int. Cl.
| | |
|---|---|
| *F26B 5/06* | (2006.01) |
| *A61J 1/16* | (2006.01) |
| *A61M 5/24* | (2006.01) |
| *A61M 5/00* | (2006.01) |

(52) U.S. Cl.
CPC ............. *F26B 5/06* (2013.01); *A61J 1/165* (2013.01); *A61M 5/002* (2013.01); *A61M 5/24* (2013.01)

(58) Field of Classification Search
CPC ............ F26B 5/06; A61J 1/165; A61M 5/002; A61M 5/24
USPC ...................................................... 34/66, 92
See application file for complete search history.

(56) References Cited

U.S. PATENT DOCUMENTS

| | | | |
|---|---|---|---|
| 3,199,217 A * | 8/1965 | Oldenkamp | F26B 5/06 34/92 |
| 4,060,911 A | 12/1977 | Weiler et al. | |
| 4,177,577 A * | 12/1979 | Bird | F26B 5/06 34/92 |
| 4,501,719 A | 2/1985 | Williams | |
| 4,597,188 A * | 7/1986 | Trappler | F26B 21/14 34/287 |
| 5,069,670 A | 12/1991 | Vetter et al. | |
| 5,320,603 A | 6/1994 | Vetter et al. | |
| 5,438,838 A * | 8/1995 | Sitte | F17C 3/085 34/294 |
| 5,689,898 A | 11/1997 | Renzi | |
| 5,884,413 A * | 3/1999 | Anger | F26B 5/06 34/92 |

(Continued)

FOREIGN PATENT DOCUMENTS

| | | | | |
|---|---|---|---|---|
| CA | 2571232 C | * | 2/2010 | ............... C08J 9/28 |
| EP | 1771503 B1 | * | 9/2014 | ............... C08J 9/28 |

(Continued)

*Primary Examiner* — Stephen M Gravini
(74) *Attorney, Agent, or Firm* — Howson & Howson LLP (57) ABSTRACT

A carrier for supporting containers such as syringes or cartridges in a lyophilization chamber during lyophilization of substances contained therein, comprises a base assembly with an array of holes for receiving the containers. Each hole includes a heat-conductive metal portion for engagement with lower parts of the container held therein and a relatively non-conductive polymeric portion surrounding a portion of the container above the lower portion for enhancing the vertical growth of relatively large ice crystals. An upper part of the carrier supported above the base assembly includes a plunger-holding plate for frictionally holding elastomeric plungers and a pusher plate movable toward the plunger-holding plate and having protrusions for pushing the plungers out of the plunger-holding plate and into the containers before the containers are removed from the chamber.

10 Claims, 8 Drawing Sheets

(56) References Cited

U.S. PATENT DOCUMENTS

| | | | |
|---|---|---|---|
| 5,964,043 A | 10/1999 | Oughton et al. | |
| 6,068,874 A * | 5/2000 | Grocholski | A23B 4/031 |
| | | | 34/196 |
| 6,920,701 B2 * | 7/2005 | Haseley | F26B 5/06 |
| | | | 34/92 |
| 7,467,482 B2 | 12/2008 | Yarborough et al. | |
| 8,096,971 B2 | 1/2012 | Bassarab et al. | |
| 8,371,039 B2 | 2/2013 | Kuu et al. | |
| 8,544,665 B2 | 10/2013 | Bogle et al. | |
| 8,677,649 B2 | 3/2014 | Böttger et al. | |
| 8,726,619 B2 | 5/2014 | Bogle et al. | |
| 8,793,896 B2 * | 8/2014 | Patel | G01N 21/68 |
| | | | 34/290 |
| 8,950,609 B2 | 2/2015 | Aneas | |
| 8,984,763 B2 * | 3/2015 | Savarese | F26B 17/023 |
| | | | 34/266 |
| 9,003,676 B2 * | 4/2015 | Yarborough | A61M 5/002 |
| | | | 34/287 |
| 9,121,637 B2 * | 9/2015 | Ling | F26B 5/06 |
| 9,528,761 B2 * | 12/2016 | Kuu | F25D 17/02 |
| 9,625,210 B2 | 4/2017 | Kuu et al. | |
| 9,739,532 B2 * | 8/2017 | Baugh | F26B 5/06 |
| 9,869,513 B2 * | 1/2018 | Kuu | F26B 5/06 |
| 10,113,797 B2 * | 10/2018 | Dern | F26B 23/001 |
| 10,451,346 B1 * | 10/2019 | Nguyen | F26B 5/065 |
| 10,767,925 B2 * | 9/2020 | Capeder | F26B 3/00 |
| 10,809,003 B2 * | 10/2020 | De Beer | F26B 5/06 |
| 10,921,058 B2 * | 2/2021 | Nguyen | A23L 3/44 |
| 2001/0008962 A1 | 7/2001 | Forsberg et al. | |
| 2005/0086830 A1 | 4/2005 | Zukor et al. | |
| 2012/0248057 A1 | 10/2012 | Bogle et al. | |

FOREIGN PATENT DOCUMENTS

| | | | | |
|---|---|---|---|---|
| JP | 6496303 B2 * | 4/2019 | | A61M 5/5086 |
| WO | WO-2006010273 A1 * | 2/2006 | | C08J 9/28 |
| WO | WO-2016124213 A1 * | 8/2016 | | A61P 25/04 |

* cited by examiner

APPARATUS FOR LYOPHILIZATION OF PRODUCTS CONTAINED IN PRODUCT DELIVERY UNITS

FIELD OF THE INVENTION

This invention relates to the preparation and packaging of pharmaceutical products, and more particularly to an apparatus for supporting an array of product delivery units, such as cartridges or syringes, in a lyophilization chamber in such a way as to achieve improved efficiency in the lyophilization process. Another aspect of the invention is a feature, associated with the supporting apparatus, for closing the cartridges or syringes following completion of lyophilization and before removal from the lyophilization chamber.

BACKGROUND OF THE INVENTION

Lyophilization, or "freeze-drying," is a process by which a solvent, usually water, is removed from a material, by direct conversion of the solvent from a solid state to vapor, i.e., without intermediate conversion of the solvent to a liquid. The material is placed in a chamber, and cooled by conduction to effect freezing of the water content so that ice crystals are formed. The chamber is then evacuated to effect sublimation of the ice crystals in a primary drying stage, and the water vapor is collected by a condenser in communication with the chamber. Lyophilization requires the application of an amount of heat corresponding to heat of fusion as well as heat of vaporization, but, in contrast to other drying methods, the temperature at which the drying occurs is well below ambient temperatures, so that the ice crystals remain in a solid condition, and water, or other solvent, present in the material as a solid, is removed as a vapor without being converted to a liquid. Later, in a secondary drying stage, warmer temperatures are applied to desorb water from the dried product while the pressure in the chamber is maintained at the reduced level or even further reduced. In some processes, the chamber pressure may be increased in secondary drying after all of the ice is sublimed in the primary drying stage.

In the case of pharmaceutical products, the process is typically carried out by placing an array of vials containing the product to be lyophilized in the lyophilization chamber on a stainless steel heat-exchange shelf formed with internal channels though which a liquid heat transfer medium flows. The size and shape of the vials is such that heat can be transferred relatively efficiently, from the material in the vials to the shelf surface during the freezing step, and from the shelf to the vials for sublimation during primary drying and desorption during secondary drying.

Although lyophilization is commonly carried out using vials, it is desirable to carry out lyophilization in a "pre-filled" device, i.e., a container that, as supplied to the practitioner, is already filled with a predetermined dosage. Such devices include pre-filled syringes, and cartridges, i.e., containers that are inserted into a reusable or disposable apparatus for dispensing of the contained substance. A special auto-injector configured to receive cartridges is an example of such an apparatus. The pre-filled containers can be "dual chamber" cartridges or syringes, that contain both a dried product and a diluent separated by an elastomeric septum such as a plunger.

One difficulty encountered in carrying out lyophilization in cartridges and syringes is that the geometry of the cartridge or syringe is different from that of a vial of the kind typically used for lyophilization. A typical lyophilization vial is much wider than a syringe or cartridge, which allows a significant portion of the vial to reside in direct contact with the shelf. Cartridges and syringes typically have a narrow, elongated, tubular shape, and, when placed in lyophilization chamber, cartridges will have their crimped ends, which have the least surface area, in proximity to the lyophilizer shelf. Similarly, syringes will have their needle assembly covers in proximity to the lyophilizer shelf. The length of the syringes and cartridges inherently makes them narrower. This affects the height of the resulting fill volume, and therefore the distance of their contents away from the shelf and the distance the solvent vapor needs to travel from the sublimation front, through the dried layer, to the top to escape from the solid material or "cake." Thus, the increased height of the fill volume leads to longer drying times. Further, because of the elongated shape of the cartridge or syringe, a portion farther away from the shelf acts as a heat exchanger in proximity to a non-temperature controlled environment. These two factors inhibit efficient processing in cartridges and syringes, and also in dual chamber devices. In addition, because most of the contents of the cartridges or syringes are far from the lyophilizer shelf, it is difficult to maintain a uniform temperature and to achieve effective heat transfer during freezing and drying. The narrow, elongated shape of the cartridges and syringes also impedes the movement of water vapor through the material in the sublimation and desorption stages. The shape of the cartridges and syringes alone does not inhibit mass transfer (i.e., the movement of water vapor) directly, but rather the shape indirectly inhibits mass transfer since the resulting increased height makes it harder for water vapor at the bottom of the container to escape through the longer cake distance. The shape also limits the overall net heat transfer indirectly, since the taller container allows absorption of heat from the environment, and the absorbed heat warms the product, limiting how low a temperature can be achieved during the freezing and primary drying steps. Further, the passageway for the water vapor by or through a plunger insertion mechanism and plunger above the container can inhibit mass transfer.

Providing a lyophilization shelf with deep sockets to receive the cartridges or syringes potentially provides better heat transfer. However, when the lower parts of the syringes or cartridges are surrounded by metal (usually stainless steel), ice crystals tend to grow not vertically, but horizontally. Moreover, the ice crystals tend to be smaller when grown in a syringe or cartridge surrounded by metal. The horizontal, and smaller, ice crystals impede vapor transmission during sublimation, reduce the rate of sublimation, and can extend the time required to carry out the lyophilization process by a matter of days. Thus, whereas the primary drying stage of the lyophilization process in containers having a short vertical region of contact between the container and the surrounding metal can be carried out typically in a matter of a few days, e.g., three days, the time required for primary drying in the case of a longer vertical region of contact can be considerably longer, e.g., nine days.

There is another problem with lyophilization in a cartridge or syringe for use as a "pre-filled" device and designed for use with an elastomeric plunger that seals the product. If the plunger is inserted before the lyophilization process is commenced, the syringe or cartridge must be in an orientation for filling and placement on the lyophilization shelf such that the material in the cartridge or syringe is farther from the shelf. On the other hand, if the plunger is to be inserted after the lyophilization process is completed, the cartridge or syringe is removed from the protective environment of the lyophilization chamber. Uptake of environmental moisture during the interval between removal from the chamber and insertion of the plunger can lead to decreased product quality, and exposure to ambient pressure can be detrimental to the function of the syringe or the medical device in which the cartridge is used.

SUMMARY OF THE INVENTION

The invention is essentially a carrier for supporting an array of tubular containers on a shelf of a lyophilization chamber. However, the invention can also be considered to be a lyophilization apparatus comprising the carrier in combination with a lyophilization chamber and an array of tubular containers, e.g. cartridges or syringes, containing the material that is to be subjected to lyophilization.

The lyophilization chamber has a shelf for supporting a carrier, and includes means for drawing heat away from a carrier supported on said shelf, e.g., a channel within the shelf for conducting a flowing heat transfer fluid. The shelf functions as a heat exchanger, removing heat by cooling during freezing, and supplying heat during primary drying (sublimation) and during secondary drying (desorption). The carrier supports the array of tubular containers, and is removably received on the shelf.

The carrier comprises a container-supporting plate having a top surface, and a set of recesses extending downward from the top surface. Each of the recesses receives one of the tubular containers and comprises a polymeric upper portion surrounding and engaging an intermediate portion of the tubular container received therein, and a metallic lower portion engaged both with a lower portion of the same tubular container and with the shelf of the lyophilization chamber. The metallic lower portions conduct heat from the tubular containers to the shelf during freezing, and from the shelf to the tubular containers during drying, while the polymeric upper portions of the recesses provide thermal shielding for the intermediate portions of the tubular containers during freezing, primary drying and secondary drying. The thermal shielding achieves a more uniform temperature in the material being lyophilized even though, because of the narrow, elongated, configuration of the containers, some of the material is remote from the lyophilization shelf. The thermal shielding avoids the formation of horizontal ice crystals and the formation of smaller ice crystals, both of which are detrimental to the removal of water vapor during sublimation. The polymeric upper portions of the recesses also ensure that all of the containers in the array are subjected to substantially the same temperature.

The container-supporting plate can be composed of a polymeric upper layer and a metallic lower layer, the lower layer having an upper surface engaged with a lower surface of the polymeric layer. In this case, each of the container-receiving recesses extends through the polymeric upper layer and at least part way through the metallic layer from the upper surface thereof. Alternatively, the container-supporting plate can be composed of a polymeric material having metallic tubes fitted into lower portions of container-receiving recesses formed in the polymeric material.

The carrier can include a plunger plate disposed above the container-supporting plate and a pusher plate disposed above the plunger plate. A set of posts supports the plunger plate in fixed, spaced, relationship to the container-supporting plate. The plunger plate has an array of plunger-receiving holes, and each of the recesses in the container-supporting plate is aligned with a plunger-receiving hole in the plunger plate. The pusher plate has a set of downward protruding elements for pushing plungers held in the plunger-receiving holes of the plunger plate into the tubular containers received in the recesses of the container-supporting plate. Each of the plunger-receiving holes in the plunger plate is associated with, and receives, one of the downward protruding elements, and the pusher plate is movable relative to the plunger plate in a direction to cause the downward protruding elements to extend through their associated plunger-receiving holes and to push plungers held in the plunger-receiving holes into tubular containers received in the recesses of the container-supporting plate. The pusher plate can be pressed downward, by a pushing mechanism provided in the lyophilization chamber, to insert plungers into the tubular containers following completion of the freeze-drying process but before the lyophilization chamber is opened.

The plunger plate has a downward-facing surface capable of contacting upper ends of the tubular containers. This downward-facing surface can have a channel associated with, and extending laterally from, each of the through holes. These channels allow passage of water vapor emitted from openings at the upper ends of the tubular containers while plungers are disposed in the plunger-receiving holes of the plunger plate.

As an alternative, or in addition to, the horizontal channels, each of the plunger-receiving holes can have its cylindrical side wall formed with least one channel extending along the length of the side wall, for allowing passage of water vapor emitted from an opening at the upper end of one of the tubular containers past a plunger disposed in the plunger-receiving hole.

DETAILED DESCRIPTION OF THE PREFERRED EMBODIMENTS

Figure 1:
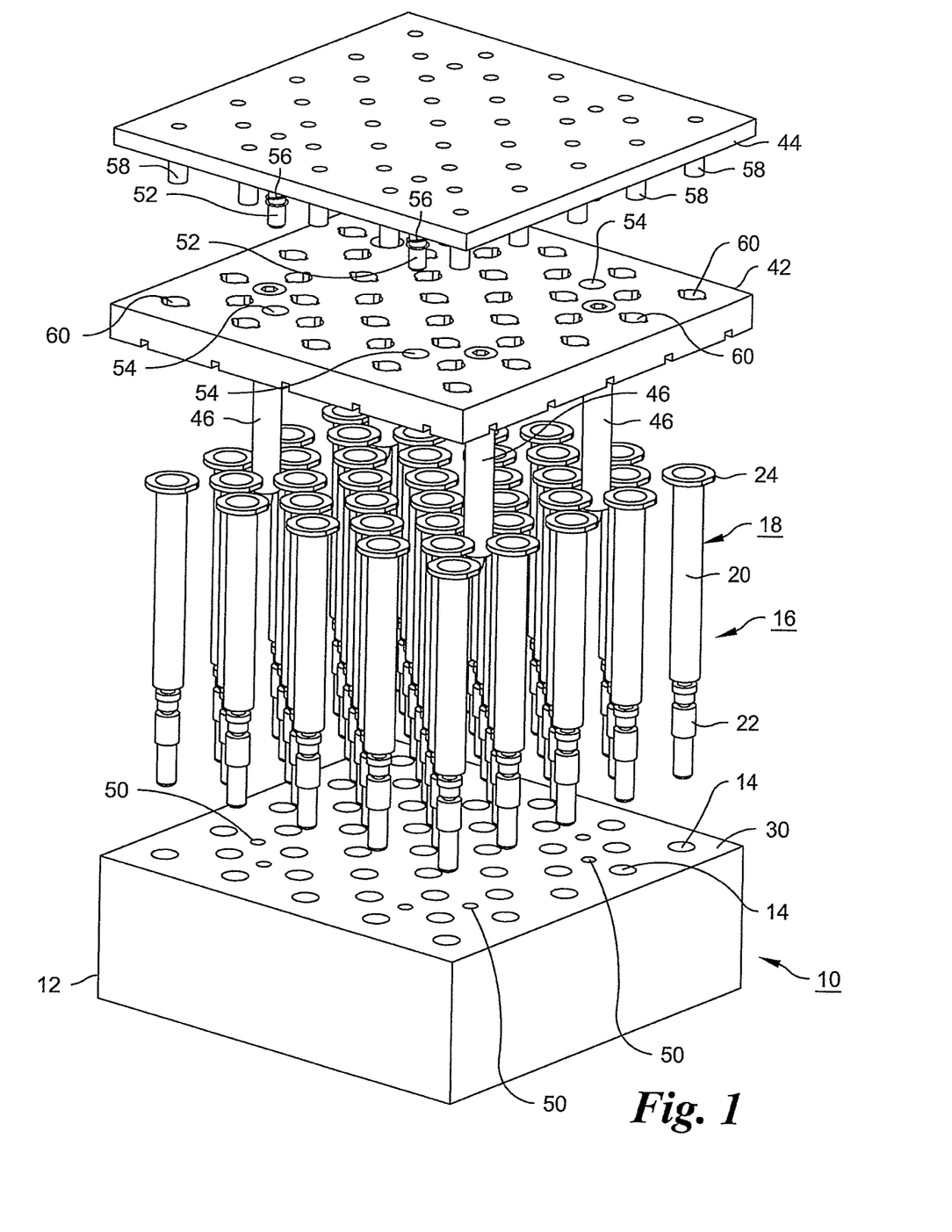
FIG. 1 is an exploded perspective view of a syringe carrier for supporting an array of syringes during lyophilization, the carrier being viewed from a level above the level of the upper part thereof.
Figure 2:
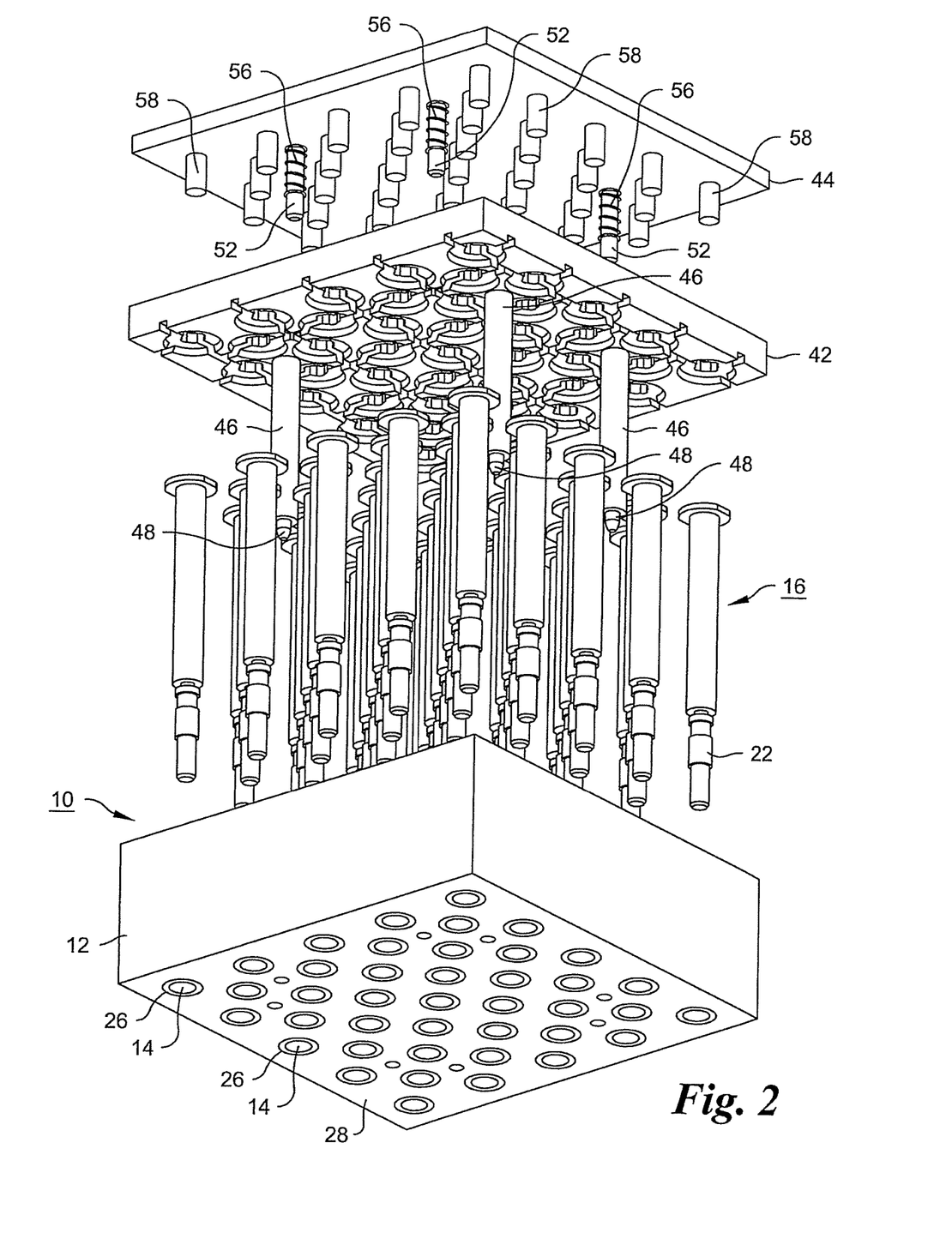
FIG. 2 is an exploded perspective view of the syringe carrier of FIG. 1, viewed from a level below the level of the lower part thereof.

The syringe carrier shown in FIGS. 1 and 2 comprises a base assembly 10 comprising a polymeric plate 12 composed of Poly Ethyl-Ethyl Ketone (PEEK), for example, and formed with an array of holes, e.g., holes 14, each for receiving an end portion of one syringe of an array 16 of syringes. Each syringe comprises a syringe body, a needle connected at one end of the syringe body and located inside a removable protective cover, and a flange at the opposite end of the syringe body. Thus, as shown in FIG. 1, syringe 18 comprises a body 20, a protective needle cover 22 enclosing a needle (not shown), and a finger-engageable flange 24 for engagement with fingers of the individual administering an injection.

Figure 3:
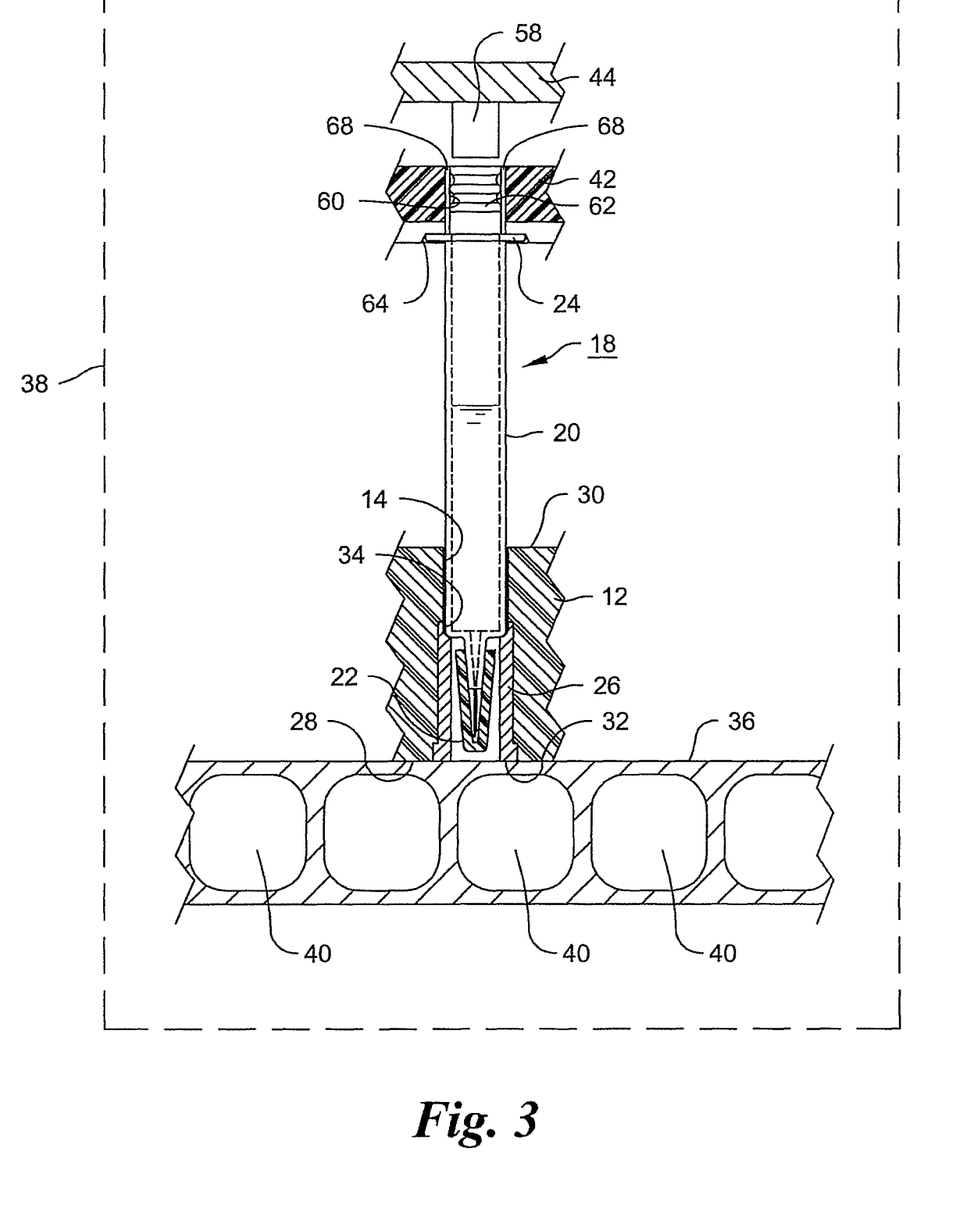
FIG. 3 is a vertical sectional view of a portion of the syringe carrier of FIGS. 1 and 2, showing a syringe in place and showing a plunger positioned for insertion into the body of the syringe, and includes a schematic representation of a lyophilization chamber and a lyophilization shelf.

As shown in FIGS. 2 and 3, each of the holes 14 of the polymeric plate 12 is fitted with a heat-conductive metal tube 26 composed of stainless steel, for example. As shown in FIG. 3, the metal tube 26 extends part way through the polymeric plate 12, from the bottom face 28 of the plate to an intermediate location between the bottom face 28 and the top face 30. The lower end of each tube 26 is preferably flush with the bottom face 28 of the polymeric plate, and formed with a flange 32 for engagement with the surface of a lyophilization chamber shelf over an area sufficient to ensure adequate heat conduction between the metal tube and the shelf. Optionally, the flanged lower ends of the tubes can extend below the bottom face 28 of the plate.

The tubes 26 can be fitted to the holes in the polymeric plate in any of various ways, but are preferably secured in the holes 14 in the process of molding the plate.

As shown in FIG. 3, the size of each of the holes 14 in the polymeric plate is such that it fits the syringe body 20 while allowing insertion and removal of the syringe from the hole. Preferably, the size of each hole 14 is such that there is a narrow gap between the wall of the hole 14 and the syringe body therein. This gap limits heat transfer by radiation and by conduction. It also allows for proper alignment of the tube for plunger insertion and also allows for expansion and contraction over the range of temperatures utilized in the lyophilization process.

The upper end of each of the metal tubes 26 is formed with a recess 34 shaped to engage the shoulder of the syringe body so that the syringe body contacts the metal tube over an area sufficient to provide for efficient, location specific, conduction of heat, from the syringe and through the metal tube, to the shelf 36 of the lyophilization chamber 38. Ice crystals grow in a direction opposite to the direction in which heat is removed. The engagement of the recess 34 with the shoulder of the syringe body therefore also aids in controlling the direction of heat transfer during freezing, so that the ice crystal grow in a direction from the shoulder of the syringe or cartridge in the plate 12 toward the top 30 of the plate. Channels 40 in the shelf, for the flow of heat transfer fluid, are shown in FIG. 3.

The carrier shown in FIGS. 1, 2 and 3 also includes a plunger-insertion section composed of a plunger-holding plate 42 and a "pusher" plate 44. The plunger-holding plate 42 is supported from the polymeric plate by a set of four posts 46. Three such posts are visible in FIGS. 1 and 2. The posts 46 are fixed to, and extend downward from, the plunger-holding plate 42, and are formed with projections 48 (FIG. 2) at their lower ends that are receivable in holes 50 (FIG. 1) in the upper face 30 of the polymeric plate 12, allowing the plunger-insertion section to be removed from the base assembly for insertion and removal of the syringes from the carrier.

Cylindrical guide pins 52, fixed to, and extending downward from, the pusher plate 44, extend slidably into holes 54 in the plunger-holding plate 42. Compression springs 56, surrounding the guide pins 52, engage the upper face of the plunger-holding plate 42, and normally support the pusher plate at a location spaced above the plunger-holding plate 42. These springs are compressed by movement of the shelves of the lyophilization chamber at the end of the drying process to insert the plungers into the syringes.

The pusher plate 44 is formed with an array of downward-protruding pushing projections 58, and the plunger holding plate 42 is formed with a corresponding array of plunger-receiving holes 60. The number and arrangement of the pushing projections 58 and plunger-receiving holes 60 corresponds to the number and arrangement of the syringe-receiving holes 14 in the base assembly. When the guide pins 52 are inserted into holes 54 in the plunger-receiving plate 42, each of the pushing projections 58 is aligned with one of the plunger-receiving holes 60.

The upper part of each plunger-receiving hole 60 is cylindrical, and of a size adapted to hold an elastomeric plunger frictionally by imparting a small amount of radial compression to the plunger. As shown in FIG. 3, a plunger 62, which may be formed with a series of axially spaced annular ribs, is held frictionally in the cylindrical upper part of one of the plunger-receiving holes 60, and engageable by one of the pushing projections 58 when the pusher plate 44 is pressed downward to push the plunger into the open upper end of a syringe.

Figure 4:
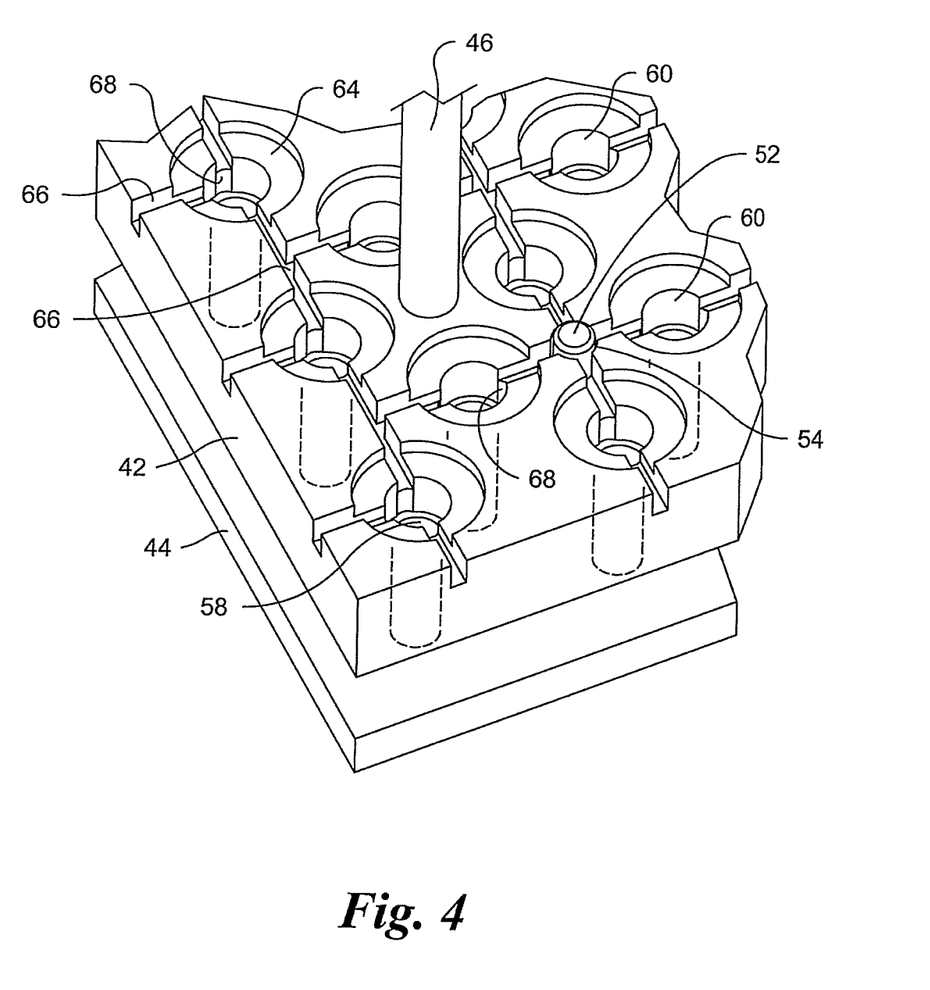
FIG. 4 is a perspective view showing a portion of the bottom face of the plunger-holding plate in FIGS. 1 and 2, with the plunger-holding plate inverted to provide a clearer view of the relationship of the holes, recesses and channels formed in the plate.

As shown in FIGS. 3 and 4, the bottom side of the plunger-receiving plate 42 is formed with a recess 64 surrounding the lower opening of each hole 60. The position of each of these recesses 64 is such that it can readily receive the flange 24 at the upper end of one of the syringes in the array 16 of syringes while the lower portions of the syringes extend into holes 14 in the base assembly. The recesses are tapered, and fit the flanges of the syringes in such a way that, when the syringes are placed in the base assembly and the plunger-receiving plate is thereafter set in place by the engagement of its supporting posts 46 with the base assembly 10, the syringes are positioned to receive the plungers in their open upper ends when the pusher plate is pressed downward. The tapered recesses in the underside of the plunger-receiving plate facilitate placement of the plunger plate on the array of syringes held in the base assembly by accommodating small departures from uniformity in the array of syringes. As the plunger-receiving plate is set into place, the tapered recesses ensure alignment of the openings at the upper ends of the syringes with the plungers 62.

As shown in FIG. 4, and also in FIG. 2, an array of horizontally extending channels 66, formed in the underside of plunger-receiving plate 42, includes portions that intersect the recesses 64, and also includes portions that extend to the edges of the plate 44, to allow for flow of vapor out of the syringes during the lyophilization process while the plungers are in place in holes 60 in the plunger-receiving plate 42. FIGS. 3 and 4 also show that each of the plunger-receiving holes is formed with two opposed vertical channels 68, which provide additional paths for the flow of vapor out of the syringes when the plungers are in place in holes 60. The vertical channels 68 can be used as alternatives to, or in addition to, the horizontal channels 66.

With each of the syringes in the array 16 arranged as shown in FIG. 3, in the carrier, the carrier is placed on a shelf in a lyophilization chamber and lyophilization takes place in the usual manner in three successive steps: solidification by freezing, sublimation (or "primary drying"), and desorption ("secondary drying").

In the freezing step, a heat transfer fluid (HTF), chilled by liquid nitrogen or by mechanical refrigeration, is circulated through passages 40 within a shelf 36 on which the carrier is placed. Freezing of the liquid in the syringes begins with nucleation, and nucleation is followed by the growth of ice crystals. In lyophilization using conventional vials, which are typically shorter and wider than a syringe, ice crystals grow vertically, i.e., in a direction away from the cold surface on which the vials are placed. In the case of a syringe, however, which tends to be long and narrow, the vertical distance from the area of contact between the syringe body and the surface where heat exchange takes place slows the formation of ice crystals. Moreover, if this area of contact is increased by deepening the hole in the heat exchange medium so that a greater portion of the syringe body is surrounded by the metal heat exchange medium, ice crystals will form more quickly, but will tend to grow horizontally and impede sublimation. The horizontal ice crystals and the distance from the upper part of the material in the syringe to the shelf, in combination, retard mass transfer in the sublimation process.

In the carrier depicted in FIGS. 1-4, except for a small portion of the syringe body engaged with the metal tubes 26, a lower portion of the syringe body is surrounded by the polymeric material of the plate 12, which controls ice crystal formation during the freezing step, thereby producing larger, vertical, ice crystals which allow more efficient removal of water vapor during primary and secondary drying. The larger ice crystals also have a lesser tendency to inhibit mass transfer, and consequently allow for more evaporative cooling, which results in a lower product temperature during sublimation. The sublimed ice crystals in the upper portions of the material in the syringe bodies provide for passage of water vapor from ice crystals in the lower portions of the syringe bodies that are subsequently sublimed. The polymeric material of the base assembly also shields the product within the syringe from warmer temperatures during the freezing and primary drying steps. In short, the principal objective of the configuration of the metal tubes and the polymeric plate is to foster growth of the ice in the vertical direction instead of in the horizontal direction.

In the utilization of the syringe, the freeze-dried material can be dissolved in a solvent drawn inward through the needle a short time before the administration of an injection Alternatively, the syringe can be utilized as a "two-part" syringe by pushing the plunger inward to an intermediate location within the syringe, introducing the solvent into the syringe at a location above the plunger, sealing the solvent by introducing another plunger, and providing a by-pass mechanism for combining the solvent with the freeze-dried material. The by-pass mechanism can be, for example, an outwardly extending channel in the wall of the syringe, through which the solvent flows past the lower plunger. Alternatively, the by-pass mechanism can be a by-pass needle that extends upward from the lower end of the syringe and penetrates the lower plunger when pressure is applied to the sealing plunger causing the lower plunger to move downward. The by-pass needle has an opening that allows the solvent to flow into contact with the freeze-dried material.

Figure 5:
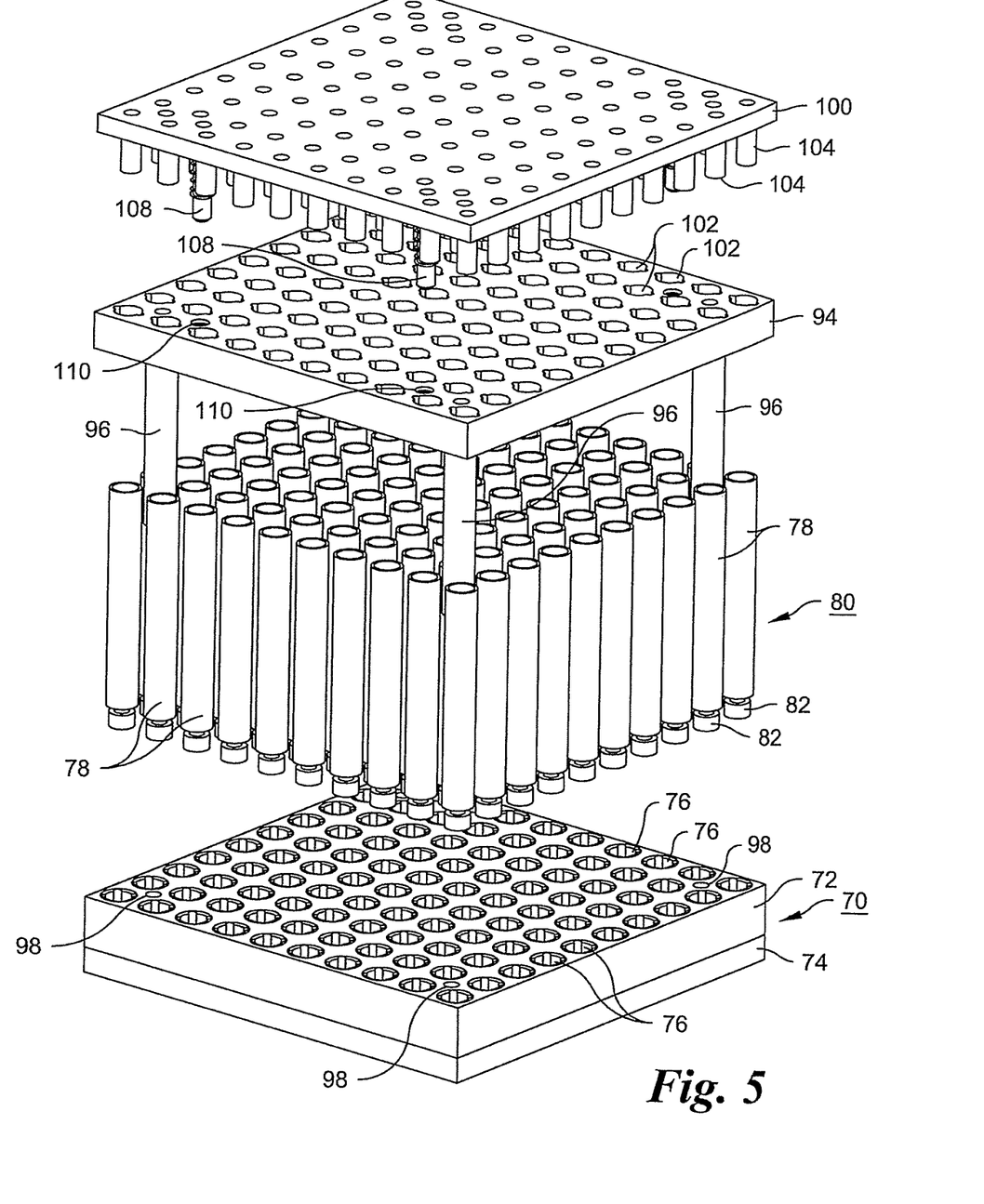
FIG. 5 is an exploded perspective view of a cartridge carrier for supporting an array of cartridges during lyophilization, the carrier being viewed from a level above the level of the upper part thereof.
Figure 6:
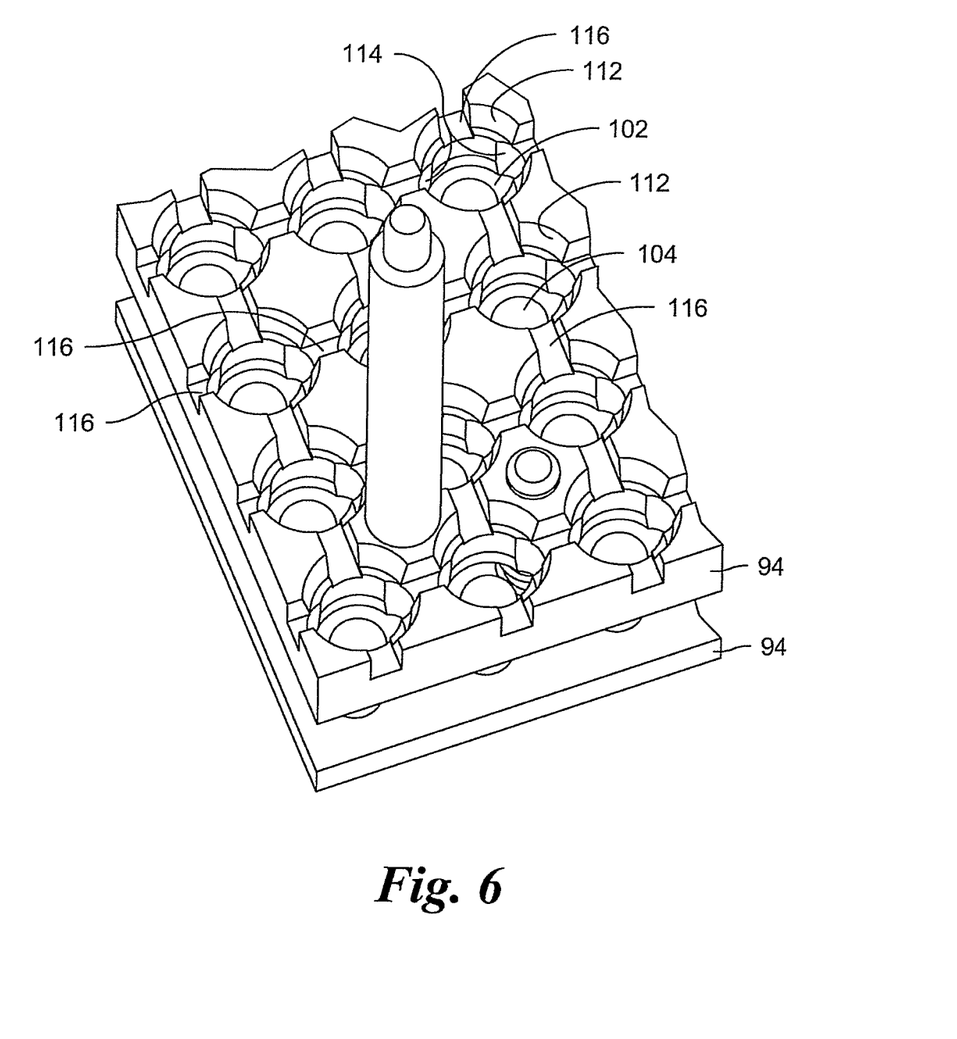
FIG. 6 is a perspective view showing a portion of the bottom face of the plunger-holding plate of the carrier in FIG. 5.
Figure 7:
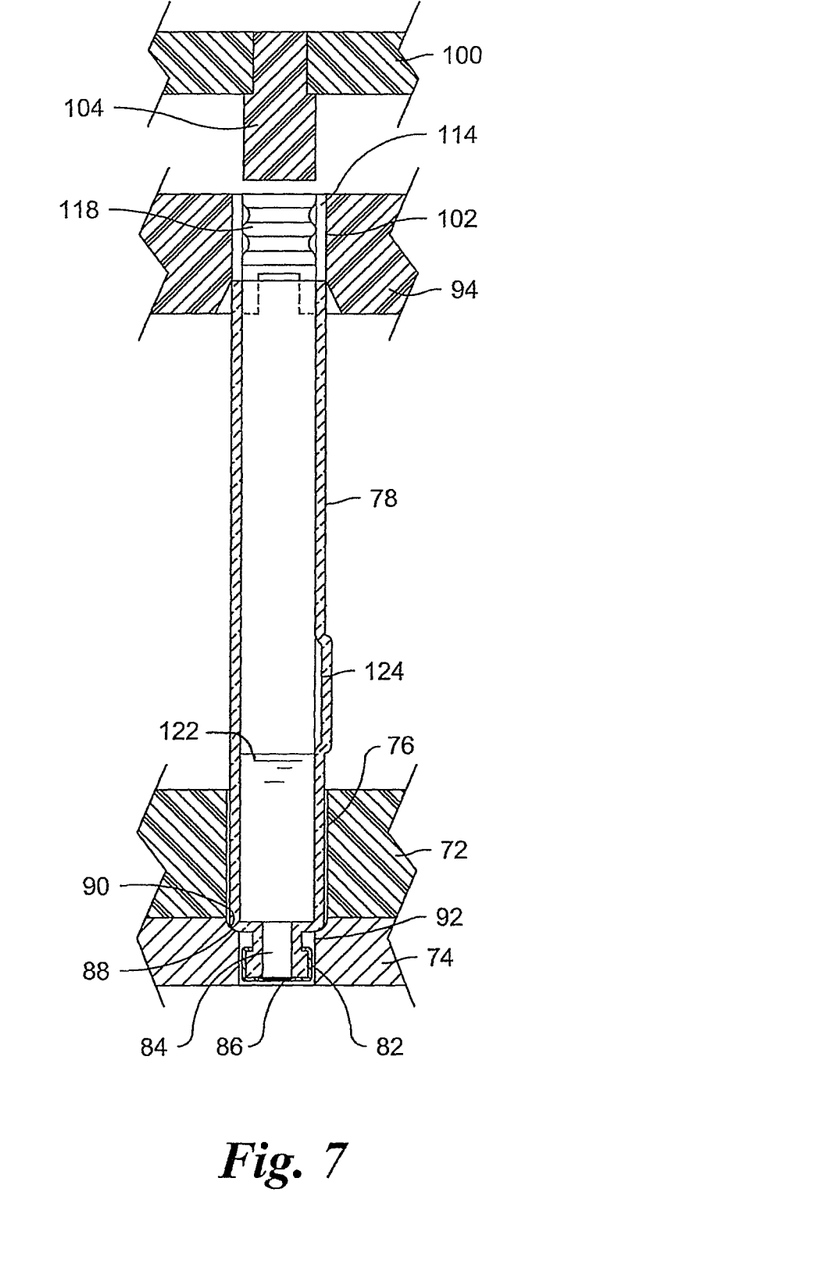
FIG. 7 is a vertical sectional view of a portion of the cartridge carrier of FIG. 5, showing a cartridge in place and showing a plunger positioned for insertion into the body of the cartridge.

The embodiment illustrated in FIGS. 5-7 is utilized for lyophilization of materials in cartridges, which are inserted into injectors, i.e., reusable, manually or automatically operated devices used for administering injections. This embodiment is similar to the embodiment illustrated in FIGS. 1-4, the principal differences being the number and arrangement of the containers, i.e., the cartridges, and the structure of the base assembly. The cartridges are arranged in rows and columns, each row consisting of the same number of cartridges as every other row, and each column consisting of the same number of cartridges as every other column. The base assembly is composed of an upper polymeric plate and a lower metallic plate having aligned cartridge-receiving holes, instead of being composed of a polymeric plate with metal tubes extending part-way through holes in the polymeric plate.

The polymeric and metallic plates can be secured together by any suitable means, such as pins (not shown) extending upward from the metallic plate and received in holes formed in the underside of the polymeric plate. If the diameters of the holes in the polymeric plate are slightly less than the diameters of the pins the extend upward from the base plate, the pins can be held in the holes by compression of the polymeric material. Alternatively, the two plates can be secured together by other means such as screw fasteners. The metallic base plate and the insulating polymeric plate above it direct the heat flux, and provide insulation from extraneous heat sources during the drying steps.

As shown in FIG. 5, the base assembly 70 consists of a polymeric plate 72, composed, for example, of PEEK (Poly Ethyl-Ethyl Ketone), and a metal plate 74, preferably composed of stainless steel, joined with the polymeric plate 72 on the underside thereof. The base assembly in FIG. 5 has a 10×10 array of cartridge-receiving holes 76, each for receiving one cartridge 78 of an array 80 of one-hundred cartridges.

Each of the cartridges 78 is in the form of an elongated glass tube having an open upper end and having a metal cap 82 fitted to a narrow neck at its lower end. The cap 82 includes an opening 84, shown in FIG. 7, closed by a membrane 86 that is punctured by a needle in the syringe or other injection instrument into which the cartridge is inserted. As shown in FIG. 7, the glass tube of the cartridge body extends through a hole 76 in the polymeric plate 72 and a short distance into the metallic plate 74, until a shoulder 88 of the glass tube engages an annular ledge 90 in a hole 92 extending through the metallic plate. The diameter of the portion of hole 92 below the ledge 90 is preferably only slightly larger than the outer diameter of the metal cap 82 of the cartridge.

Returning to FIG. 5, the carrier for the cartridges includes a plunger-holding plate 94, supported from the base assembly 70 by four posts 96, which have projections (not shown) at their lower ends that removably fit into holes 98 in the upper face of the polymeric plate, thereby allowing the plunger-holding plate and a pusher plate 100, associated with the plunger-holding plate, to be lifted away from the base assembly for insertion and removal of the cartridges.

The plunger-holding plate 94 has an array of holes 102 for holding elastomeric plungers, and downward-protruding pushing projections 104 are provided on the underside of the pusher plate 100, each such projection being positioned so that it can extend into one of holes 102. Pins 108, three of which are visible in FIG. 5, extend slidably into holes 110 formed in the plunger-holding plate, and are surrounded by coiled compression springs that support the pusher plate in spaced relationship to the plunger-holding plate while allowing the pusher plate to be urged downward to cause the projections 104 to push the plungers into the upper ends of the cartridges.

As shown in FIG. 6, the underside of the plunger-holding plate 94 is formed with recesses 112. Each recess 112 surrounds one of the plunger-receiving holes 102, and is tapered, with its narrow upper end of size such that it closely fits the upper end of one of the cartridges, allowing for accurate alignment of plungers with the openings at the upper ends of the cartridges when the plunger-holding plate 94 is sent into place.

Opposed, axially-extending channels 114 allow for flow of vapor out of the cartridges during the lyophilization process. The vapor then flows through the axially-extending channels 114 outward to the upper side of the plunger-holding plate and also through horizontal channels of an array of horizontal channels 116, formed on the underside of plate 94, which either extend from one of the recesses to an adjacent recess or extend from one of the recesses to an edge of the plate 94.

Figure 8:
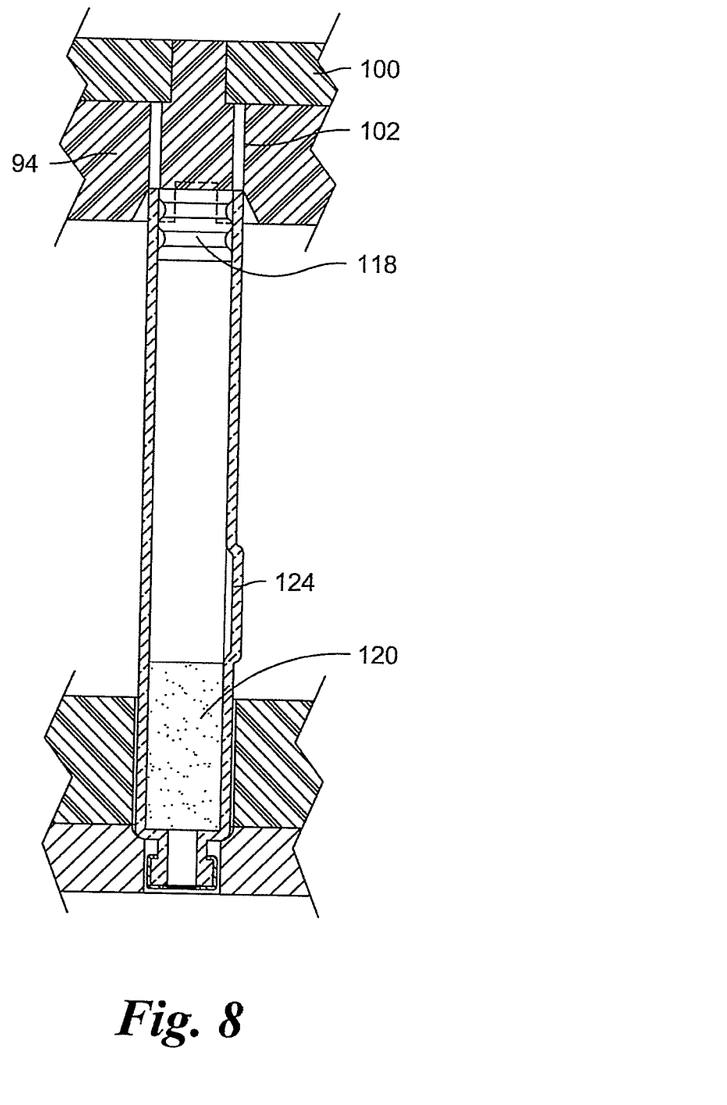
FIG. 8 is a vertical sectional view of the portion of the cartridge carrier of FIG. 5, showing the plunger inserted into the cartridge.

FIG. 7 shows an elastomeric plunger 118 held frictionally in a hole 102 in plate 100 and a projection 104 on the underside of pusher plate 100 positioned to push the plunger into the opening at the upper end of the cartridge 78. FIG. 8 shows the plunger 118 being pushed into place in the cartridge following completion of the lyophilization process.

In the lyophilization process, the volume of freeze-dried material 120, as shown in FIG. 8, is the same as the volume of liquid 122 (FIG. 7) in the cartridge prior to freezing unless there is shrinkage of the cake during drying. The mass of the freeze-dried material 120, however, is less than the mass of the liquid 122 because of the removal of water in the drying steps of lyophilization. A by-pass channel 124 is formed in the wall of the cartridge at an intermediate location along the length of the cartridge above the level of the dried material 120.

Following completion of lyophilization, the plunger can be pushed downward into the interior of the cartridge, to a position at which it is above the location of the by-pass channel. Thereafter, a liquid solvent in which the solid, freeze-dried material is to be dissolved immediately prior to the administration of an injection, is introduced into the space above the plunger, and another plunger is inserted to close off the cartridge, trapping the solvent liquid between the plungers. When the injection is to be administered, the plunger nearest the upper end of the cartridge is pushed downward causing the liquid between the plungers to exert pressure on the lower plunger, thereby forcing it into the space adjacent the by-pass channel. When the lower plunger is in that position, the solvent can flow through the by-pass channel and mix with and dissolve the freeze-dried material, forming a liquid that can be made to flow through a needle inserted through the membrane 86 (FIG. 7) by further movement of the two plungers.

A by-pass channel, as in the embodiment of FIGS. 5-8, can also be utilized with two plungers in the syringes of the embodiment shown in FIGS. 1-4 as an alternative to other means for allowing the solvent to mix with the freeze-dried material.

By using the plunger holding and insertion apparatus as described above it is possible to remove air, or to control the atmosphere and pressure in cartridges or syringes, and then seal the cartridges or syringes with the atmosphere therein at a controlled pressure and composition.

Various modifications can be made to the carriers shown in FIGS. 1-8. For example the number and arrangement of the syringe- or cartridge-receiving holes in the base assemblies 10 and 70 can be modified. The base assembly can be utilized with other kinds of plunger-holding and pushing assemblies. Various other modifications can be made to the apparatus described above, without departing from the scope of the invention as defined in the following claims.

What is claimed is:

1. A lyophilization apparatus comprising:
   a lyophilization chamber having a shelf for supporting a carrier, and including means for drawing heat away from a carrier supported on said shelf;
   an array of tubular containers each containing a material to be lyophilized; and
   a carrier, removably received on said shelf, for supporting said array of tubular containers, the carrier comprising a container-supporting plate having a top surface, said plate having a set of recesses extending downward from said top surface, each of said recesses receiving one of said tubular containers of said array and comprising a polymeric upper portion surrounding and engaging an intermediate portion of one of said tubular containers, and a metallic lower portion engaged with a lower portion of said one said tubular containers and also engaged with said shelf;
   said metallic lower portions conducting heat from said tubular containers to said shelf; and
   said polymeric upper portions of said recesses providing thermal shielding for said intermediate portions of said tubular containers.

2. The lyophilization apparatus according to claim 1, in which said plate comprises a polymeric upper layer and a metallic lower layer, the lower layer having an upper surface engaged with a lower surface of the polymeric layer, and in which each of said recesses extends through said polymeric upper layer and at least part way through said metallic layer from the upper surface thereof.

3. The lyophilization apparatus according to claim 1, further comprising:
   a plunger plate disposed above said container-supporting plate, a set of posts supporting said plunger plate in fixed, spaced, relationship to said container-supporting plate, said plunger plate having an array of plunger-receiving holes, and each of said recesses in said container-supporting plate being aligned with a plunger-receiving hole in said plunger plate; and
   a pusher plate disposed above said plunger plate, said pusher plate having a set of downward protruding elements for pushing plungers held in said plunger-receiving holes of the plunger plate into tubular containers received in said recesses in the container-supporting plate, each of said plunger-receiving holes in the plunger plate being associated with, and receiving, one of said downward protruding elements, and said pusher plate being movable relative to said plunger plate in a direction to cause said downward protruding elements to extend through their associated plunger-receiving holes and to push plungers held in said plunger-receiving holes into tubular containers received in said recesses in the container-supporting plate.

4. The lyophilization apparatus according to claim 3, wherein said plunger plate has a downward-facing surface capable of contacting upper ends of said tubular containers, said downward-facing surface having a channel associated with, and extending laterally from, each of said through holes, said channels allowing passage of water vapor emitted from openings at the upper ends of said tubular containers while plungers are disposed in said plunger-receiving holes.

5. The lyophilization apparatus according to claim 3, wherein each of said plunger-receiving holes has a cylindrical side wall, said cylindrical side wall being formed with least one channel extending along the length thereof for allowing passage of water vapor emitted from an opening at the upper end of one of said tubular containers past a plunger disposed in the plunger-receiving hole having said cylindrical side wall.

6. A carrier for supporting an array of tubular containers on a shelf of a lyophilization chamber, the carrier comprising a container-supporting plate having a top surface, said container-supporting plate having a set of recesses extending downward from said top surface for receiving tubular containers of material to be lyophilized, each of said recesses being capable of receiving a tubular container of said array and comprising a polymeric upper portion capable of surrounding and engaging an intermediate portion of one of said tubular containers, and a metallic lower portion engageable with a lower portion of said one said tubular containers and engageable with an upward facing surface of a shelf of a lyophilization chamber.

7. The carrier according to claim 6, in which said plate comprises a polymeric upper layer and a metallic lower layer, the lower layer having an upper surface engaged with a lower surface of the polymeric layer, and in which each of said recesses extends through said polymeric upper layer and at least part way through said metallic layer from the upper surface thereof.

8. The carrier according to claim 6, further comprising:
a plunger plate disposed above said container-supporting plate, a set of posts supporting said plunger plate in fixed, spaced, relationship to said container-supporting plate, said plunger plate having an array of plunger-receiving holes, and each of said recesses in said container-supporting plate being aligned with a plunger-receiving hole in said plunger plate; and
a pusher plate disposed above said plunger plate, said pusher plate having a set of downward protruding elements for pushing plungers held in said plunger-receiving holes of the plunger plate into tubular containers received in said recesses in the container-supporting plate, each of said plunger-receiving holes in the plunger plate being associated with, and receiving, one of said downward protruding elements, and said pusher plate being movable relative to said plunger plate in a direction to cause said downward protruding elements to extend through their associated plunger-receiving holes and to push plungers held in said plunger-receiving holes into tubular containers received in said recesses in the container-supporting plate.

9. The carrier according to claim 8, wherein said plunger plate has a downward-facing surface capable of contacting upper ends of said tubular containers, said downward-facing surface having a channel associated with, and extending laterally from, each of said through holes, said channels allowing passage of water vapor emitted from openings at the upper ends of said tubular containers while plungers are disposed in said plunger-receiving holes.

10. The carrier according to claim 8, wherein each of said plunger-receiving holes has a cylindrical side wall, said cylindrical side wall being formed with least one channel extending along the length thereof for allowing passage of water vapor emitted from an opening at the upper end of one of said tubular containers past a plunger disposed in the plunger-receiving hole having said cylindrical side wall.

* * * * *